United States Patent
Jockel et al.

(10) Patent No.: US 9,904,998 B2
(45) Date of Patent: Feb. 27, 2018

(54) PATIENT-SPECIFIC AND AUTOMATIC X-RAY SYSTEM ADJUSTMENT BASED ON OPTICAL 3D SCENE DETECTION AND INTERPRETATION

(71) Applicant: KONINKLIJKE PHILIPS N.V., Eindhoven (NL)

(72) Inventors: Sascha Andreas Jockel, Hamburg (DE); Christoph Kurze, Hamburg (DE); Dirk Manke, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 344 days.

(21) Appl. No.: 14/422,240

(22) PCT Filed: Aug. 26, 2013

(86) PCT No.: PCT/IB2013/056895
§ 371 (c)(1),
(2) Date: Feb. 18, 2015

(87) PCT Pub. No.: WO2014/033614
PCT Pub. Date: Mar. 6, 2014

(65) Prior Publication Data
US 2015/0228071 A1  Aug. 13, 2015

Related U.S. Application Data

(60) Provisional application No. 61/693,367, filed on Aug. 27, 2012.

(51) Int. Cl.
*A61B 6/08* (2006.01)
*G06T 7/00* (2017.01)
(Continued)

(52) U.S. Cl.
CPC .............. *G06T 7/0012* (2013.01); *A61B 6/08* (2013.01); *A61B 6/544* (2013.01); *A61B 6/545* (2013.01);
(Continued)

(58) Field of Classification Search
CPC ........... A61B 6/06; A61B 6/08; A61B 6/4464; A61B 6/527; A61B 6/544; A61B 6/545;
(Continued)

(56) References Cited

U.S. PATENT DOCUMENTS 5,917,883 A  6/1999  Khutoryansky et al.
6,272,368 B1  8/2001  Alexandrescu
(Continued)

FOREIGN PATENT DOCUMENTS

WO  2006038165 A1  4/2006

OTHER PUBLICATIONS

Arun et al, "Least-Square Fitting of Two 3-D Point Sets", IEEE Transactions on Pattern Analysis and Machine Intelligence, vol. PAMI-0, No. 5, 1987, p. 698-700.
(Continued)

*Primary Examiner* — Irakli Kiknadze

(57) ABSTRACT

An apparatus (130) and method for automatically or semi-automatically controlling a collimator (COL) of an x-ray imager (100) to collimate imager (100)'s x-ray beam and adjusting an alignment of the x-ray imager (100) in respect of an object (PAT). The collimation and alignment operation is based on 3D image data (3DI) of the object (PAT) to be imaged. The 3D image data (3DI) is acquired by a sensor (S). The sensor (S) operates on non-ionizing radiation. The 3D image data (3DI) describes a shape in 3D of the object (PAT) and anatomic landmarks are derived therefrom to define a collimation window (W) for a region of interest (ROI). Based on the collimation window (W) the collimator
(Continued)

(COL)'s setting and imager (100) alignment is adjusted accordingly.

24 Claims, 3 Drawing Sheets

(51) Int. Cl.
G01B 11/25 (2006.01)
G06T 3/00 (2006.01)
H04N 13/02 (2006.01)
G06T 7/70 (2017.01)
G06T 7/50 (2017.01)
A61B 6/06 (2006.01)
A61B 6/00 (2006.01)

(52) U.S. Cl.
CPC .............. G01B 11/254 (2013.01); G06T 3/00 (2013.01); G06T 7/50 (2017.01); G06T 7/70 (2017.01); H04N 13/0203 (2013.01); A61B 6/06 (2013.01); A61B 6/4464 (2013.01); A61B 6/527 (2013.01); G06T 2207/10116 (2013.01)

(58) Field of Classification Search
CPC ......... A61B 6/12; A61B 6/4441; A61B 6/469; A61B 6/504; A61B 6/466; A61B 6/032; A61B 6/4233; A61B 6/481; A61B 5/055; A61B 6/487; A61B 2034/107; A61B 2090/364; A61B 2090/376; A61B 5/7289; A61B 6/022; A61B 6/025; A61B 5/0064; A61B 6/102; A61B 6/4291; A61B 6/542; A61B 6/589; G01B 11/254; G06T 2207/10116; G06T 3/00; G06T 7/0012; G06T 7/004; G06T 7/0051; G06T 7/50; G06T 7/70; H04N 13/0203; G01N 27/3272
USPC .............. 378/62, 195, 206, 95, 20, 207, 209
See application file for complete search history.

(56) References Cited

U.S. PATENT DOCUMENTS

| 7,494,276 | B2 | 2/2009 | Borgmann et al. |
| 7,831,013 | B2* | 11/2010 | Star-Lack .............. A61B 6/025 378/23 |
| 2003/0081734 | A1 | 5/2003 | Nicolas et al. |
| 2008/0101538 | A1 | 5/2008 | Schliermann |
| 2009/0096783 | A1 | 4/2009 | Shpunt et al. |
| 2009/0285357 | A1 | 11/2009 | Khamene et al. |
| 2012/0116374 | A1 | 5/2012 | Jia et al. |

OTHER PUBLICATIONS

Besl, "A Method for Registration of 3-D Shapes", IEEE Transactions on Pattern Analysis and Machine Intelligence, vol. 14, No. 2, 1992, p. 239-256.
Fung et al, "Evaluation of the Increase of Radiation Absorbed Dose in Critical Organs of the Patient Due to Poor Beam Collimation in Chest and Lumbar Spine X-Ray Examinations", 11th Int'l Congress of the International Radiation Protection Association, Madrid, Spain: The Hong Kong Polytechnic University, 2004, 1 Page.
Anguelov et al, "SCAPE: Shape Completion and Animation of People", ACM Trans. Graph, vol. 24, No. 3, 2005, pp. 408-416.
Scharstein et al, "High-Accuracy Stereo Depth Maps Using Structured Light", Proceedings of the IEEE Conference on Computer Vision and Pattern Recognition, 2003, p. 195-202.
Weiss et al, "Home 3D Body Scans From Noisy Image and Range Data", Computer Vision (ICCV), IEEE International Conference, 2011, p. 1951-1958.
Kinect Biomechanics: Part 1, http://engineeringsport.co.uk/2011/05/09/kinect-biomechanics-part-1/, Downloaded Feb. 18, 2015.

* cited by examiner

PATIENT-SPECIFIC AND AUTOMATIC X-RAY SYSTEM ADJUSTMENT BASED ON OPTICAL 3D SCENE DETECTION AND INTERPRETATION

CROSS-REFERENCE TO PRIOR APPLICATIONS

This application is the U.S. National Phase application under 35 U.S.C. § 371 of International Application Serial No. PCT/IB2013/056895, filed on Aug. 26, 2013, which claims the benefit of U.S. Application Ser. No. 61/693,367, filed on Aug. 27, 2012. These applications are hereby incorporated by reference herein.

FIELD OF THE INVENTION

The present invention relates to radiation based imaging and in particular to a control apparatus, to a control method, to an imaging system, to a computer program element and to a computer readable medium.

BACKGROUND OF THE INVENTION

Appropriate x-ray beam collimation is important when using an x-ray imager.

X-ray beam collimation to the relevant anatomy reduces the amount of ionizing radiation to which a patient is exposed and thus minimizes radiation risks. Furthermore, appropriate collimation reduces the amount of scattered radiation since less volume is irradiated which results in an improved detail contrast and image quality.

For the acquisition of, for example, a chest x-ray, the current collimation workflow requires a lab technician to usher the patient to imager's x-ray detector, and to adjust detector and x-ray tube to the appropriate height and adjust collimator's setting. The technician then leaves the examination room and releases x-ray exposure. Time measurements revealed that approximately ⅓ of the time in an imaging session is taken up by appropriate patient and system positioning including collimation.

U.S. Pat. No. 7,494,276 describe a system for assisting an operator in operating an x-ray device.

SUMMARY OF THE INVENTION

There may therefore be a need for an alternative apparatus to ease the burden on medical personnel when adjusting imagers either in preparation of or during an image acquisition session or run.

The object of the present invention is solved by the subject matter of the independent claims where further embodiments are incorporated in the dependent claims. It is understood that the following aspect of the invention equally applies to the control method, to the imaging system, to the computer program element and to the computer readable medium.

According to a first aspect of the invention there is provided a control apparatus comprising:

an input port for receiving 3D image data sensed by a sensor in a 3D survey of an object whilst said object resides between an imager's x-ray source and said imager's x-ray detector. The 3D image data so received includes spatial depth information that varies with the object's outer surface. The 3D image data is descriptive of the object's shape in 3D;

a 3D image data analyzer configured to compute from the received 3D image data anatomical landmark data of the object to so obtain imager control data to control said imager;

a control unit configured to use the computed control data to control operation of said x-ray imager before or during image acquisition of said object.

The proposed control apparatus affords patient-specific/adaptive and automatic or semi-automatic collimation and/or alignment of X-ray imager's geometry based on optical 3D scene detection and interpretation. Spatial 3D (three-dimensional) shape data of the object (for example a patient), anatomical body landmarks derived therefrom and a given x-ray imager geometry are together used to control i) patient-specific collimation to a desired anatomy of interest and/or ii) patient specific imager alignment (such as tube and detector orientation relative to patient) and/or exposure lock to avoid x-ray exposure during patient movement.

No markers need be applied to the patient's body during the image acquisition. The patient walks into the examination room "as is" and towards a desired target spot therein. Either automatically or upon request by the imager operator, the sensor resumes its detection operation. The 3D shape and geometry of the patient's 3D contours are then used to detect the anatomic landmarks such as limbs, torso, neck, head, shoulder, overall body height, overall body width, etc. Depending on the type of x-ray image to be taken, the or some of the identified landmarks along with their position coordinates which are also derivable form the sensed 3D image data, are then used to define a collimation window in 3D space.

According to one embodiment the patient's body is 3D surveyed in its entirety in an alternative embodiment the 3D survey is only partial for example restricted to patient's torso. Gesture and or posture recognition may also be used to distinguish between patient and a medical staff who happens to be present during image acquisition as is often the case in x-ray supported interventions such as cardiac vessel treatments. According to one embodiment, the computed control data includes demarcation data demarcating an imager window for a region of interest of said object.

According to one embodiment the 3D image data analyzer operates to update the imager window during when movement of the object is detected or upon user request, the updated imager window thereby following the object's movement, the control unit using the updated imager window to control imager's image acquisition during the object's movement. The sensor is configured to track object's movement in three spatial dimensions. According to one embodiment there is a user-actuatable "one-button" functionality for adapting the collimation window right before release of x-ray.

According to one embodiment the 3D image data analyzer is configured to establish position data of the anatomic landmarks of the object. The demarcation data is based on said anatomic landmark position data. In other words, position of internal organs or anatomies of interest are deduced from external clues such as mutual spatial arrangement and shape of the outer anatomic landmarks. According to one embodiment there is a database or look-up table where specific landmarks are associated with different x-ray exams types. Once the user supplies a specification of the exam type such as "chest x-ray", a description of the relevant landmarks can be retrieved and used for detecting the landmark position in the 3D image data. The landmark positions are then used as demarcation data for the collimation window.

According to one embodiment the object is a human or animal body, the landmark position data indicative of the positions of a plurality of joints of the human or animal body or of other anatomical landmarks as identifiable as a characteristic variation of the spatial depth information such as limbs, head, neck portion, shoulder portion or other arrangements of body parts.

According to one embodiment the 3D image data is used for skeleton recognition. In one embodiment, for a thorax or chest x-ray, hip joints and shoulder joints are identified from the depth values making up the 3D image data and the line joining the two hip joints is used as a lower demarcation for the collimation window. The line joining shoulder joints is the upper demarcation with the two torso flanks forming the lateral demarcation. Using data base accessible expert medical knowledge and statistical anatomic data gathered from a large number of patients the matching of the computed window can be assessed and adjusted by using for instance a scoring scheme. A high score indicates that the computed window corresponds well to the instant patient data (age, sex, etc.). The expert data is either user supplied or apparatus is configured to connect to a database to retrieve same. Variations in patient's anatomies can be accounted for thus increasing the robustness of the collimation window computation. The knowledge can then be used to trim the computed collimation window. In the thorax embodiment, using the computed demarcations as a reference frame the upper two third portion is then used as the actual collimation window because this is where the lungs can be expected to be located. In other words, the collimation window as computed from the landmarks may be fine-tuned by the apparatus to known organ positions for a given organ of interest. In other embodiments the collimation window as demarked by the landmarks is used without further fine-tuning.

According to one embodiment controlled imager operation includes i) a collimation operation for a beam emanating from said X-ray source and/or includes ii) an alignment of the x-ray tube and/or of the detector relative to the object and/or adjustment of x-ray source XR's operation voltage kVp and/or mAs (milli-Ampere seconds) and/or exposure time and/or dosage. The operation voltage can be set in response to patient's physiognomy, in particular patient thickness, as evidenced by depth information in the 3D image data. In other words the kVp setting is adjusted to vary directly with patient's thickness.

According to one embodiment the 3D image data is acquired by exposure of the sensor to non-ionizing radiation. This allows reducing patient's dosage. No x-ray pre-shot is required to align imager and in particular to adjust imager's collimator According to one embodiment the sensor is part of a ranging camera. Examples are Microsoft Kinect or ASUS Xtion Pro Live equipment.

According to one embodiment the sensor uses a predefined structured light pattern, projected onto the patient or object to sense the 3D image data. According to one embodiment the structured light pattern is a speckle pattern. According to one embodiment infrared light is used but using light in the visible spectrum is also envisaged. The proposed apparatus affords improving clinical workflow because no user interaction is required for the actual collimation or imager alignment (e.g. tube and detector). The imager settings are adapted to the patient's size and/or thickness which in turn mean a reduced number of workflow steps for the medical staff in the ever busier clinical environments. Even staff with little radiological education can in principle operate x-ray imagers safely and efficiently.

The patient benefits in that the number of retakes can be cut down due to an avoidance of erroneous collimations thereby furthering the ALARA ("As Low As Reasonably Achievable") objective. The radiologists can enjoy better image quality due to less scatter radiation because of premium collimation and imager alignment settings.

Definitions

"3D image data" is acquired by a sensor responsive to non-ionizing radiation or sound. The 3D image data is an array of pixels each pixel having a position in said array and a value. Each pixel position corresponds to a position of a point on the object's surface and the value is directly related to or can be expressed in terms of a distance between camera's sensor and said object surface point. Pixel values vary with sensor-object distance. Point cloud representation of the 3D mage data set is also envisaged.

"Imager setting" includes "imager geometry/alignment data" and "collimator setting data".

"Imager geometry/alignment data" is a set of angular or rectangular coordinate positions that describe a spatial configuration of the x-ray imager at any given time. The imager geometry is dependent on the particular image equipment used but comprises in general adjustable patient's bed (if any) height, position in space of detector and x-ray tube. Any given imager geometry defines the relative position between patient, detector, x-ray and collimator and the sensor position.

"Collimator setting data" is defined by the size and shape of an aperture through which x-ray beam can pass through the collimator. The aperture in turn is defined by the relative spatial positions of a plurality of collimator's blades or shutters.

"Imageable space" or "interspace of imager" or "imager's domain" is the portion of space (in general part of the examination room) where an object to be imaged must reside during image acquisition. In other words, there is at least one imager geometry setting so that primary x-ray beam is capable of irradiating said objet when in said interspace. No image can be taken if object is resident outside the imager's interspace.

BRIEF DESCRIPTION OF THE DRAWINGS

Exemplary embodiments of the invention will now be described with reference to the following drawings wherein:—

DETAILED DESCRIPTION OF EMBODIMENTS

Figure 1:
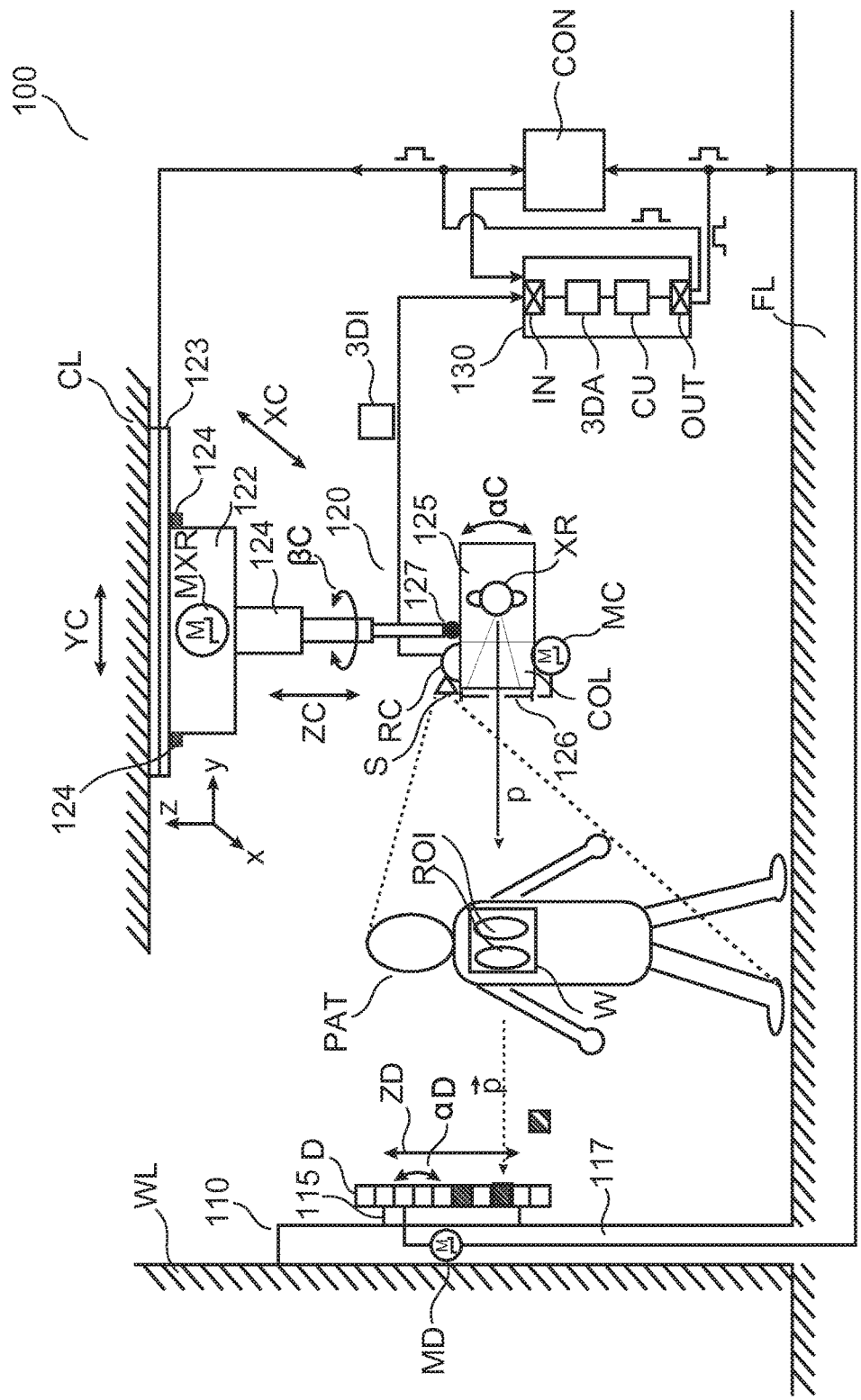
FIG. 1 shows a side elevation of an x-ray imager arrangement.

In FIG. 1 there is shown an imager arrangement according to one embodiment. X-ray imager 100 is arranged in an examination room. The examination room is indicated schematically by floor FL, ceiling CL and one of the walls WL. Imager 100 is operable to acquire x-ray projection images at adjustable projection directions from a patient PAT. Overall operation of x-ray imager 100 is controlled by an operator from a computer console CON. Console CON is coupled to a screen or monitor (not shown) on which the acquired x-ray images or imager settings may be viewed or reviewed. An operator such as a medical lab technician can control via said console CON an image acquisition run by releasing individual x-ray exposures for example by actuating a joy stick or a pedal or other suitable input means coupled to console CON. According to a different embodiment, imager 100 is of the C-arm type and patient PAT is actually lying on an examination table rather standing.

X-ray imager 100 includes a movable detector assembly 110 and a moveable x-ray tube-collimator assembly 120 (herein after referred to as the "CX Assembly").

The assemblies are movable so that an x-ray beam generated by x-ray tube XR can be directed and adapted to a shape of a specific body part ROI ("region of interest") of patient PAT's body which needs to be examined. For example, the patient's lungs may need to be examined in a "chest x-ray" so in this case the region of interest ROI is the patient's chest. The adaptation of beam p to the outlines of the region of interest is achieved by a collimator COL once slid into a desired position relative to patient PAT by actuating movable CX assembly 120. Prior to collimator interaction, x-ray beam p emanating from x-ray tube XR is a divergent beam so in absence of collimator COL the cross-sectional dimensions of the beam p when reaching patient PAT would be much larger than the area of the desired ROI. This is unsatisfactory because patient dosage may need be increased unnecessarily and more Compton scatter occurs. The purpose of collimator COL or "beam restrictor" is to restrict dimensions of the cross section of the beam so as to match in size and shape the beam p's cross section to the region of interest ROI. In one embodiment, collimator comprises two pairs of blades 126 (only one pair is shown in elevation view of FIG. 1) or sheets ("shutters") formed from lead or tungsten or other highly radiation-opaque material. One pair is arranged perpendicularly to the other and the blades are individually addressable and movable by collimator stepper motor MC so as to restrict more or less the beam in either or two of the two dimensions depending on their relative position. In this way the beam's cross section can be shaped to match the expected two dimensional outline of the region of interest ROI. This collimator arrangement allows shaping the beam into square or rectangular form in various sizes. In another embodiment a multi-leaf collimator is used comprising instead of the four blades a large number of motor-movable slats or strips arranged in opposing relationship. A multi-leaf collimator allows forming more detailed or curvilinear shapes. Setting up the collimator COL amounts to determine how to position the blades so as to make the resulting beam cross section match the perimeter of the ROI as close as possible. In the four blade collimator embodiment, the matching of said rectangular shape to the ROI is achieved by determining blade positions for said blades 126. When the blades are energized to assume the determined positions they together define an aperture with which the smallest or a reasonably small rectangular beam cross section can be realized that still includes all of the desired ROI.

Turning now to the other components of movable CX assembly 120, said assembly 120 includes a slidable overhead carriage 122, a telescopic arm 124, and a housing 125. In said housing 125 there is arranged x-ray tube XR and collimator COL. Overhead carriage 122 is slidable and moveable along two sets of tracks 124, 123 arranged perpendicularly to each other to so afford 2-dimensional movement of overhead carriage 122 along axis x,y. X-track 122 allows movement of overhead carriage 122 along x axis whereas y-track 123 (drawn in FIG. 1 as extending vertically into the plane of the paper) allows movement along the y axis. Telescopic arm 124 is affixed to overhead carriage 122 and extends therefrom downwardly. At its lower end, telescopic arm 124 terminates in a pivot 127 to which housing 125 is affixed. In other words, CX assembly enjoys a number of degrees of freedom so as to be positioned at a wide range of desired positions relative to patient PAT. There is an actuator such as a stepper motor MXR that effects movement of overhead carriage 122 along the tracks. In practice there may be a more than one motor arranged one for each tack, or a single motor where x,y movement is caused by suitable gearing. Telescopic arm 124 is arranged to allow movement of housing 125 up and down along Z axis and rotation αC around same. Up/down movement of telescopic arm 124 and rotation around the Z axis is effected by the motor MXR or a different motor. Stepper motor(s) MXR affords changing "pitch" αC around pivot 127 and changing "yaw" βC of x-ray tube XR and collimator COL around z-axis and relative to the patient PAT. In one embodiment, pitch of tube XR and COL collimator are independently by motor MXR.

Turning now to detector assembly 110, this includes a wall-stand 117 affixed to floor FL and wall WL. According to another embodiment said wall-stand is sufficiently rigid so is arranged as a free standing structure in the room without being affixed to the wall WL. In other embodiments detector assembly is affixed to ceiling CL (instead of floor or wall) and depends therefrom.

Detector D is suitable to receive and register x-rays p emanating from x-ray tube XR. Detector D is fixed to a wall mounted carriage 115 which is slidable in Z direction in tracks integrated in wall-stand 117. There is arranged a stepper motor MD that effects said movement along the Z axis of the detector assembly the same or different motor allows changing the pitch αD. Detector D comprises detector cells each receptive to an impinging x-ray beam. In one embodiment stepper motor MD is arranged to also change detector D's pitch around x-axes and/or carriage is also slidable on a separate tracks along x-axis.

Broadly, during an image acquisition run collimated x-ray beam p emanates from x-ray tube XR, passes through patient PAT at said region ROI, experiences attenuation by interaction with matter therein, and the so attenuated beam p then strikes detector D's surface at a plurality of the detector cells. Each cell that is struck by said beam responds by issuing a corresponding electric signal. The collection of said signals is then translated by a data acquisition system ("DAS"—not shown) into a respective digital value representative of said attenuation. The density of the organic material making up the ROI, that is rib cage and lung tissue in case of a lung x-ray, determines the level of attenuation. High density material (such as bone) causes higher attenuation than less dense materials (such as the lung tissue). The so registered digital values for each x-ray p are then consolidated into an array of digital values forming an X-ray projection image for a given acquisition time and projection direction.

Now, in order to acquire the x-ray image, the imager 100 needs first to be aligned to said region of interest ROI. Imager alignment parameters include setting the above mentioned collimator setting and aligning the two assemblies relative to each other and to patient PAT by controlling the various actuators so as to the slide collimator blades and the two assemblies into position so that collimator COL can collimate beam to the ROI as described above. The collection of above mentioned positional parameters are referred to as the imager's geometry or alignment parameters or data.

The procedure of setting up and adjusting the imager geometry parameters ("alignment") was found to consume about one third of the imaging session time.

A control system is proposed herein that includes a range camera RC and a controller 130 in order to facilitate and to speed up imager geometry alignment and collimator setting procedures. Range camera RC is shown arranged on the housing 125. The range camera is coupled to controller 130. Range camera RC-control 130 arrangement allows automatically, or at least semi automatically, align the imager 100 once the presence of a patient in the "interspace" between the detector D and CX-assembly has been detected.

According to one embodiment, the imager setting operation is automatic, in that the patient's presence detection is accomplished by the camera RC-controller 130 system also. In this embodiment, the imager is in a stand-by mode and resumes operation as soon patient PAT steps into the interspace. In this embodiment, camera RC is in constant sensing mode and senses said interspace and once camera RC detects intervening patient's body, imager setting commences. In the semi-automatic operation, the patient is asked to step into (and remain) in the interspace. Once in the interspace, operator actuates an "enable" operation button or issues by other input means (touchscreen, mouse-click, pedal operation etc.) an "enable" signal and the collimator setting and/or imager's alignment commences.

Broadly speaking, to effect the imager settings, range camera RC is configured to acquire 3D image data of patient PAT by exposure of same to non-ionizing radiation. The 3D image data captures the 3D shape of the patient or at least of a part of the patient. In other words the 3D image data "follows" or describes the outer surface or perimeter of patient PAT in 3D space. Said acquired 3D image data is then fed into controller 130. Controller 130 then processes said patient 3D image data in a manner described in more detail below to output position data that define a collimation window W outlining the desired region of interest ROI such as patient PAT's lungs for a chest x-ray. Said position data is then translated into desired imager alignment data that correspond to the collimation window position data. In other words, when imager is aligned according to the translated into alignment data, emitted x-ray beam is then collimated precisely (within reasonable error margin) on said computed collimation window.

Once the collimator window W position data are computed controller 130 outputs imager control signals that correspond to the computed or desired alignment data to correct accordingly the current imager alignment. Said control signals are then interpreted by suitable driver software and hardware control signals are issued to control the various stepper motors so as to effect the desired imager geometry is assumed, that is, the various movable parts "slide" into position. Said control signals are either sent to workstation CON where the driver software runs or controller 130's output port OUT is suitably configured to interface direct with the various actuators to control same to effect the reference or desired imager alignment data.

Operation of controller 130 and camera RC will now be explained in more detail.

Operation

Controller 130 includes an input port IN, an output port OUT, a 3D image analyzer 3DA and a control unit CU.

Figure 2:
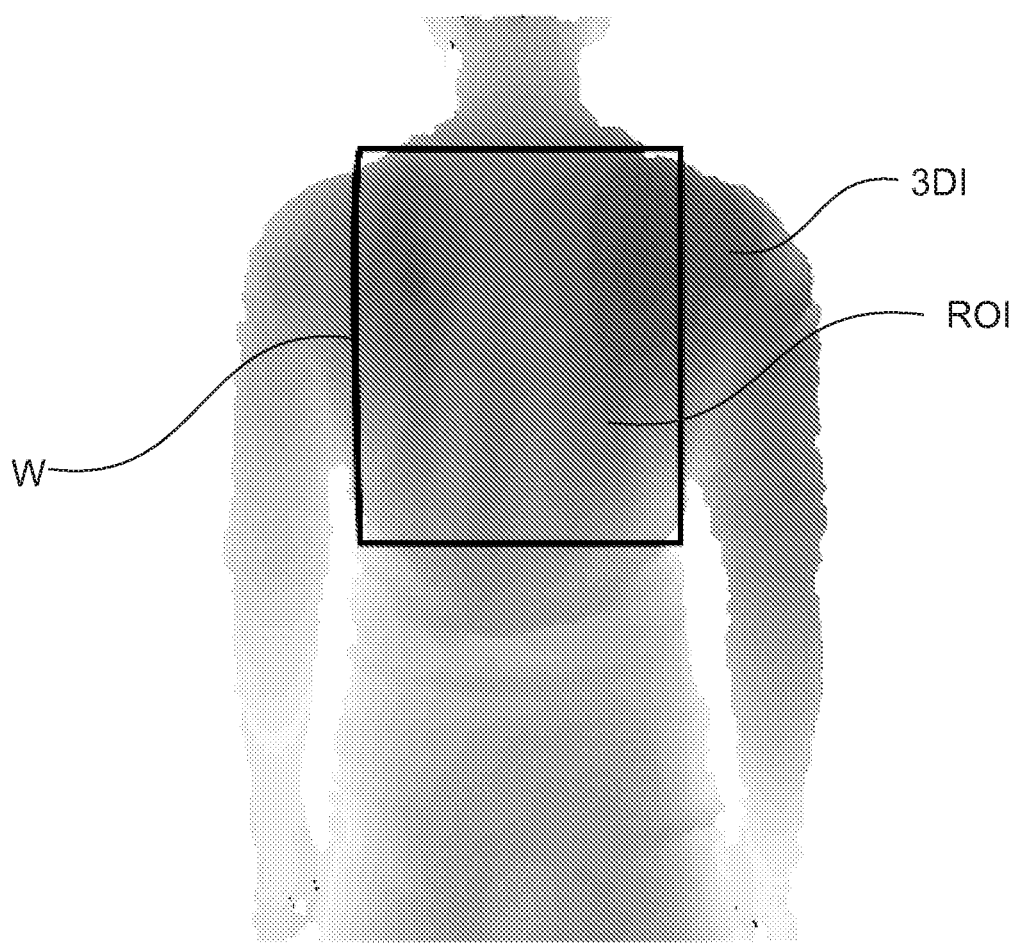
FIG. 2 shows 3D image data acquired from a patient by a sensor used in the arrangement according to FIG. 1.

With reference to FIG. 2, an example of a rendering ("2.5" dimensional distance map) of a patient 3D image data set as captured by range camera RC is shown. Grey values of the pixels vary directly with the distance of patient's surface to camera RC's sensor S. The shape of patient is clearly discernible with protruding chest showing darker because of its proximity to sensor S compared to distal hip portion.

According to one embodiment, range camera RC includes a projector that projects a cone of structured light onto patient PAT. Said structured light may for example be formed as a "speckle" pattern as described in US 2009/0096783. The reflection of said light from the patient's surface back to the camera is then registered by the sensor S likewise included in the camera. The "distortion" in the reflected speckle pattern is registered by comparison with how the speckle pattern ought to have looked like had there been no patient present. The registered distortions are then translated into a distance value for each pixel. It can also be appreciated that the censor and projector may not necessarily reside in the same camera housing as explained earlier. According to one embodiment the projector and sensor S may be arranged as different components. It is however to be understood that the range camera RC may also operate according to different principles for example time-of-flight, stereo triangulation, sheet of light triangulation, interferometry and coded aperture.

In one embodiment, the camera RC or its sensor S and/or projector are itself tiltable by operation of a suitable motor (not shown) thereby adding yet a further degree of freedom in adjusting the imager's alignment parameters/coordinates.

3D image data set 3DI is received at input port IN of controller 130. 3D image data 3DI so received is then forwarded to 3D analyzer 3DA. Because of a tracking operation by central console's CON operating system, the relative position between camera RC's sensor S and x-ray tube XR is known at all times and so is the "source to image-receptor" distance (SID). The sensor-patient surface distance as encoded by the 3D data set can be readily translated into a corresponding distance of each patient surface points to x-ray tube XR. In other words, 3D analyzer can compute the source-to-object distance (SOD). According to one embodiment, 3D image analyzer 3DA operates to calculate the position data of the collimator window W. To compute the coordinates of the collimator window, anatomic landmarks are detected based on the acquired 3D image data set.

FIG. 2 shows an example of a collimator window around the ROI for a chest x-ray. Collimator window is a rectangle circumscribing patient's chest region.

Different approaches are envisaged to detect the anatomic landmarks to so realize a patient-adaptive X-ray collimation:

According to one embodiment, a "quasi" model-less approach is used. It is based on a priori knowledge or certain presumptions about where the region of interest is situated. For example, patient's chest portion is expected in front of the detector with source-detector distance SID known which helps to identify, solely based on the shape information in the received 3D data, relevant body landmarks like shoulders and left and right torso flanks by means of the depth image. For example, 3D analyzer iterates row by row through depth values of 3D image data supplied by camera RC and once a significant change is registered the torso's flanks are assumed to have been found.

According to one embodiment body surface approximation parametric body model such as the SCAPE model is used. See for example D. Anguelov et al (2005), "SCAPE: shape completion and animation of people", ACM Trans. Graph., 24(3), 408-416. Such a model provides an accurate and scalable representation of the shape and pose of a human body. It can be used for surface matching with silhouettes derived from the sensed 3D image data. This leads to a precise description of the patient's body which can be used to locate the anatomical region of interest.

According to one embodiment a skeleton detection method is used to detect and track patient PAT's body. A body is described as a set of joint positions of a skeleton. Coordinates of the skeleton joints are the starting point for localizing the patient's chest region. Elongate structures formed by patient's extremities can be followed into the image footprint the torso so as to gain clues on where the joints are situated.

According to one embodiment, a 3D registration with an annotated, mean 3D body model is utilized. To this end, a generalized 3D body model (e.g. CT dataset) with segmented and annotated organs can be utilized to approximate the position of the relevant anatomy of the patient, e.g. lungs. The generalized 3D body model is fitted/scaled to the 3D sensed body shape of patient PAT. The fitting and scaling can be done via 3D registration techniques. The anatomical information of the generalized and scaled 3D model can then be used to identify the anatomy of interest and collimation window for the patient accordingly. See for example K. S. Arun et al (1992), "Least-Square Fitting of Two 3-D Point Sets," IEEE Transactions on Pattern Analysis and Machine Intelligence, Vol. 14, pp. 239-256, where the scaling and fitting is according to least squares.

Each of the above approaches is based on a user supplied input that allows controller 130 to identify the examination type that is the region of interest ROI. In one embodiment operator can choose a natural language string entries such as "Chest x-ray" from a menu structure in a suitable configured GUI displayed on screen. Each entry my include submenus such as "Chest x-ray"→"lung scan" and so on. In a suitable associative data structure each entry is associated with definitions in geometrical terms or otherwise for the anatomic landmarks relevant for the selected exam type. 3DA analyzer then outputs position coordinates of anatomic landmarks relevant to the instant exam type. The positions of the anatomic landmarks demarcate the collimation window W.

Once the coordinates of the collimation window are computed, operation flow passes on to control unit CU. Position coordinates parameter can be expressed in absolute spatial co-ordinates values each describing a specific position in the imager's interspace. Said collimator position data can be displayed on screen for the operator according to one embodiment. Control unit CU uses suitably programmed drivers and interface units to interface with the work station CON.

Control unit CU requests from CON the current imager geometry parameters including current collimator settings. Once current imager geometry parameters are received the desired imager geometry parameters are computed based on the coordinates of the computed collimator window W. Control unit CU then computes the desired imager parameters that would effect x-ray beam radiating only the patient area within the computed collimator window.

It should be understood that the exact coordinate description for the collimator window depends on the examination at hand and the type of collimator used. For example for the 4 blade collimator capable of shaping rectangular beam cross section, the rectangle defining said collimator window can be defined by four spatial coordinate points in the imager's interspace.

Control unit CU then compares the current imager geometry and the current collimator window with the computed desired collimator window adapted to the instant ROI of patient PAT. Correction values for the various angles and coordinates, in particular for the collimator blade positions are computed and forwarded to workstation CON. Drivers translate those coordinate correction requests into control signals which are then forwarded to the relevant stepper motors. The appropriate stepper motors are then correspondingly energized to effect the imager 100's re-alignment and collimation of collimator COL according to the desired imager geometry and the calculated desired collimator window. A corresponding "ready to expose" signal is then issued by workstation and possibly indicated visually to the operator. The x-ray projection image is either acquired automatically or the operator is to actuate first a corresponding exposure button or pedal.

According to one embodiment, the 3D image data set as received from camera RC is displayed on a screen for the operator. According to one embodiment, the calculated collimation window is displayed as an overlay on the likewise displayed rendering of the sensed 3D image data as in FIG. 2. This promotes image operation security because the human operator can check visually whether collimator window has been computed correctly. According to one embodiment, the operator feedback can also be achieved by real-time adaptation of a collimator light-field projected on the patient. In this embodiment there is lamp arranged in collimator and the light field generated by a said lamp illuminates the actual ROI so the operator can check the computed collimation prior to x-ray exposure.

According to one embodiment, x-ray imager 130 includes an exposure-lock functionality. This can be used advantageously when acquiring chest x-rays to synchronize exposure with a desired inhalation state. In this embodiment the camera RC keeps acquiring a sequence of 3D image data frames for prolonged period to track the expansion of the patient's chest during inhalation. Based on the chest shapes as recorded across the sequence of the individual 3D images, a rate of shape change can be established. Once said rate drops below a pre-defined threshold value it is assumed that inhalation is complete and a release signal is issued so as to acquire the x-ray image at that instant.

Although the patient is normally required to stand still during x-ray imaging run, the present system may also be capable of acquiring a sequence of x-ray images whilst the patient is moving during a number of image acquisitions. As long as the patient remains within the imager's interspace and as long as the motions are slow enough as compared to the system's ability to readjust via its stepping motors the imaging parameters the patient is allowed to move freely and the system upon receipt of the plurality of new 3D image data sets recalculates dynamically the ROI collimator window and the imager parameters are reset accordingly. In other words controller CON operates to produce a sequence of ROI focused collimator windows each adapted to the different patient positions. Respective imager alignment corrections are calculated and the imager's geometry is updated to follow the patient's movement.

According to one embodiment, the above mentioned imager settings also include the operating voltage of the x-ray tube XR for any given image acquisition. Said tube voltage is a function of the expected patient thickness. If more tissue is expected in to be penetrated by the beam, a higher voltage is required to maintain a given image quality. In other words according to this embodiment, controller 130 operates to adjust exposure parameters of the tube (kVp and mAs) based on the patient's thickness as derivable from the depth values in the sensed 3D image data set. The derived patient thickness at the region inside the computed collimator window is then compared with values for the settings in pre-defined lookup tables to match tube power to examination type, organ, patient thickness, height, sex, etc.

As shown in FIG. 1 the range camera RC is positioned at the collimator/x-ray housing 125. This is only according to one embodiment. In other embodiments the range camera RC is arranged on the ceiling CL, on the overhead carriage 122 or on the wall-stand 117, or on the wall W. In the embodiment where range camera RC's projector and sensor are separately housed components, the projector may be arranged on ceiling CL and it is only the sensor S that is arranged on top or below housing 125. In all embodiments, the camera is so positioned that the camera's sensor S is capable of capturing essentially the entirety of the imager's interspace or at least that portion of the interspace where the patient can be expected to reside during the image acquisition. The above described range camera and controller 130 arrangement can readily be adapted to operate for example in a C-arm x-ray imager where patient PAT is to lie on an examination table during the image acquisition rather than to stand as in FIG. 1 indicated.

The components of controller 130 are shown as integrated in one single unit. However in alternative embodiments, some or all components are arranged as separate modules in a distributed architecture and connected in a suitable communication network. Controller 130 and its components may be arranged as dedicated FPGAs or as hardwired standalone chips. In some embodiments, controller 130 or some of it components are resident in work station CON running as software routines. The components may be programmed in a suitable scientific computing platform such as Matlab® or Simulink® and then translated into C++ or C routines maintained in a library and linked when called on by work station CON.

Figure 3:
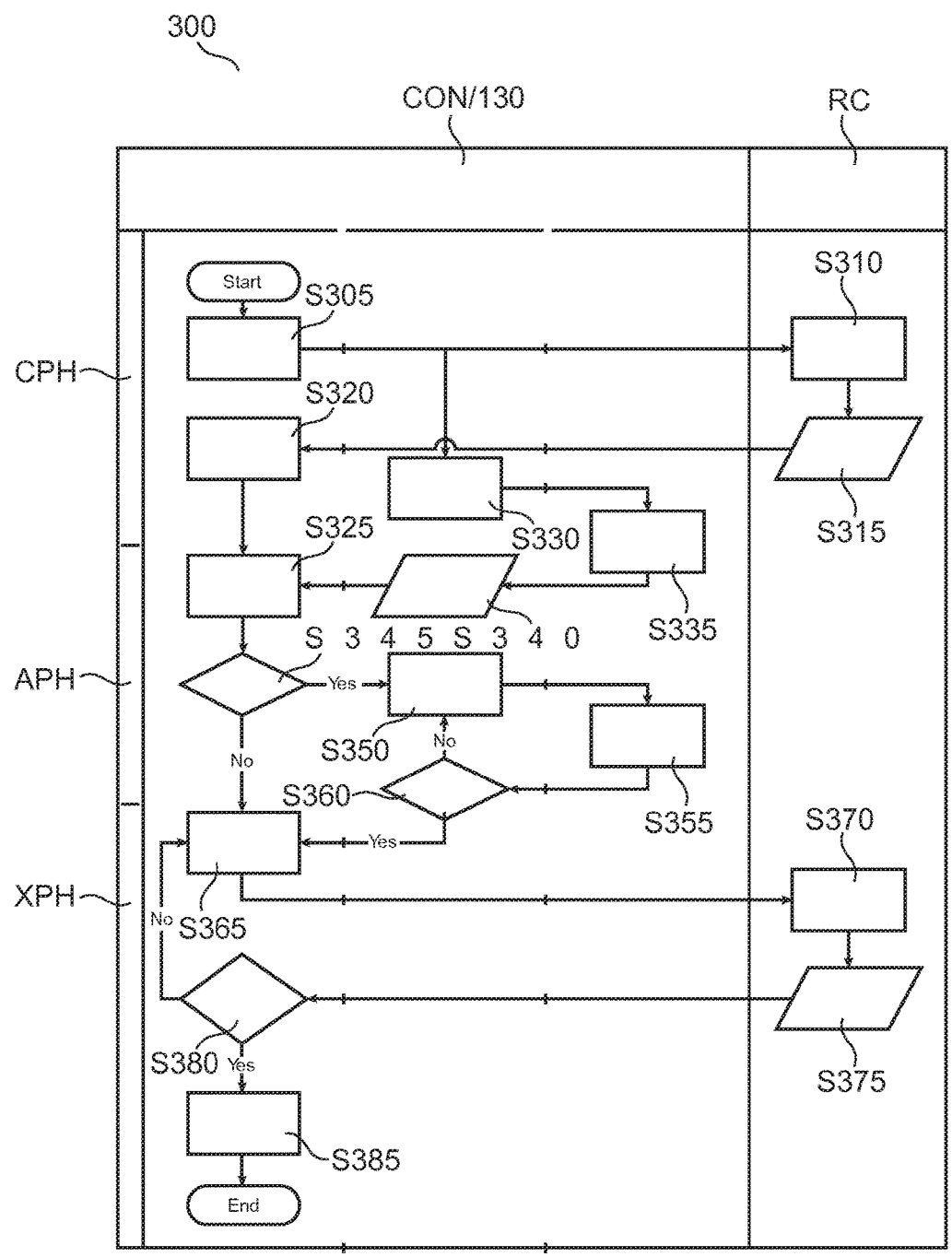
FIG. 3 shows a flow chart of a control method.

With reference to FIG. 3 a flow chart is shown for an imager 100 control method. The flow chart shows the involved system components along the horizontal axis and their interactions in different steps across different phases along the vertical axis. The phases are an automatic or semi-automatic collimation phase CPH, the imager realignment phase PH and the optional exposure-lock phase XPH.

At step S305 current imager setting is queried including current imager alignment data and current collimator setting.

At step S310 range camera acquires 3D image data from a patient residing in imager's interspace.

At step S315 the sensed 3D image data set is output and forwarded to and received by controller 130.

Controller 130 then receives at step 320 the sensed 3D image data and computes at step S320 the position data of a desired collimation window data for imager's collimator based on the 3D shape of the patient as evidenced from the received 3D image data at step S315.

At step S325 the computed collimation data is translated into desired imager alignment data. In other words, based on the computed desired collimation window a corresponding desired position data for the detector and x-ray tube are computed that, when realized, would align imager accordingly and x-ray beam would then be collimated to the computed collimation window. For the computation at step S325 of the desired imager alignment data the current imager alignment data is required which is requested at step S330 from the imager setting data queried at step S320. At step S335 the requested current alignment data is returned in response to the request by the imager 100's various actuators MD, MC, MXR and is then forwarded as current geometry data at step S340 to control unit CU.

At step S345 the computed desired alignment data corresponding to the computed collimation at S320 is compared with requested current imager geometry data. If the current imager alignment data is determined at sufficient variance with the computed desired imager alignment data, at step S350 control commands are issued by to the various stepper motors to so apply an appropriate correction to the current imager geometry.

At step S355 the geometry is realigned accordingly by actuation of the stepper motors to apply the correction.

At step 360 it is checked whether the so updated imager alignment corresponds to the desired alignment data or whether the corrected position over- or undershoots the computed desired alignment. If there is an over or undershoot, steps 350 and 355 are repeated. If the updated geometry data corresponds within a pre-defined error margin to the computed geometry data the system is appropriately realigned and flow control enters into an optional exposure lock mode. If there is no exposure lock mode or said functionality is disabled, exposure commences and an x-ray projection image is acquired.

When in exposure lock mode, it is established at step S365 on the basis of the 3D image data whether patient is in a state of maximum inhalation. To this end, range camera acquires new 3D image data at step S370 and outputs updated 3D image data at step S375. The updated 3D image is then compared with the previous 3D image data at step S380 whether patient is in a state of maximum inhalation. If no state of maximum inhalation is detected, steps S365, S370 and step S375 are repeated. If a state of maximum inhalation is detected, flow control passes to step S385 where x-ray exposure is released and the image is acquired. It will be appreciated the above described exposure lock may be linked with other or further dynamic body states. For example, exposure may be synchronized with a desired cardiac cycle rather respiration cycle whilst imager 100 is sued for an angiography imaging run.

According to one embodiment, even when not in exposure lock mode, at step S370 an updated 3D image data is acquired at user-adjustable intervals and at step S365 it is determined by comparison with the previous 3D image data whether there was patient movement. If there was patient movement, flow control is looped back to step S320 and an updated collimator window is computed and steps S320-S360 are repeated accordingly. In this way a series of collimator windows are and a corresponding series of imager re-alignment data are computed and imager re-aligned accordingly with patient movement. In other words, the collimation window is tracking the patient and imager is dynamically realigned accordingly throughout a period of patient movement.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for adjusting an X-ray image, said X-ray imager including an X-ray source, an X-ray detector, and an X-ray collimator, said apparatus comprising:
an input port for receiving three-dimensional (3D) image data sensed by a sensor in a 3D survey of an object while said object resides between said X-ray source and said X-ray detector, the 3D image data so received including spatial depth information that varies with the object's outer surface, said 3D image data descriptive of the object's shape in 3D space, said object having multiple anatomic landmarks;
a 3D image data analyzer configured: (i) to compute, from the received 3D image data, anatomical landmark data of a plurality of anatomic landmarks from among said multiple anatomic landmarks of said object to so obtain imager control data to control said imager, wherein the computed imager control data includes demarcation data demarcating an imager collimation window for a region of interest of said object; and (ii) to establish, from said received 3D image data, position data of multiple landmarks from among said plurality, wherein said demarcation data is based on the established position data;
a control unit configured to use the computed imager control data to control operation of said X-ray imager at least one of before and during image acquisition of said object,
wherein the controlling of said operation is in dynamic response to: a) the sensing by said sensor in said 3D survey, of said 3D image data from which said anatomical landmark data is computed; b) the computing of said anatomical landmark data from the received 3D image data; c) the establishing of said position data, and d) said demarcating based on said establishing, and
wherein the controlled operation of said X-ray imager includes a collimation operation for an X-ray beam emanating from said X-ray source.

2. The apparatus of claim 1, wherein said 3D image data analyzer is configured to update said imager collimation window when movement of the object is detected by sensor configured to track the object's movement in three spatial dimensions, the updated imager collimation window thereby following the object's movement, said control unit using the updated imager collimation window to control said X-ray imager during the object's movement.

3. The apparatus of claim 1, wherein the object is a human or animal body, and wherein said position data is indicative of a plurality of positions of respective joints of the human or animal body.

4. The apparatus of claim 1, wherein the control of the operation of said X-ray imager using the imager control data obtained by computing said anatomical landmark data from the received 3D image data furthermore includes an alignment, relative to said object, of at least one of said X-ray source and said X-ray detector.

5. The apparatus of claim 1, wherein said 3D image data sensed by a sensor is acquired by exposure of said sensor to non-ionizing radiation.

6. The apparatus of claim 1, further comprising a ranging camera that includes said sensor.

7. The apparatus of claim 1, further comprising a light projector and a sensor, wherein said sensor is configured to use, to sense said 3D image data, a pre-defined structured light pattern projected, by said light projector, onto said object.

8. An imager system comprising:
the apparatus of claim 1;
said X-ray imager; and
said sensor.

9. The imager system of claim 8 wherein said X-ray imager includes an X-ray tube-collimator assembly, said X-ray tube-collimator assembly comprising said X-ray source and said X-ray collimator, said sensor being arranged on said X-ray tube-collimator assembly.

10. The apparatus of claim 1, further comprising said X-ray detector, wherein said X-ray detector has a beam-receiving surface for receiving said X-ray beam, wherein, throughout said controlled operation, said X-ray detector is: a) contained in a room; and b) confined to remain oriented, for receipt of X-rays from said X-ray source, so that said beam-receiving surface faces horizontally and extends vertically.

11. The apparatus of claim 1, wherein said collimation operation controls said X-ray collimator to shape and size an aperture according to said imager collimation window.

12. The apparatus of claim 11, further comprising said X-ray collimator, said X-ray collimator including a plurality of movable collimation elements to perform the shaping and sizing, wherein the shape and size of said aperture is adapted to an outline of said region of interest, wherein said region of interest is to be irradiated by said X-ray beam, wherein said X-ray beam is projected in a direction, and wherein said outline is dependent on said direction, said elements having corresponding collimation settings, wherein said X-ray beam, upon arriving at said X-ray collimator, has a cross section, said cross section having a cross-sectional area, said collimation operation using said imager collimation window to actuate said plurality of movable collimation elements to restrict said cross-sectional area, thereby preventing a portion of the arriving X-ray beam from propagating forward toward said object and, in the restricting, matching the cross section resulting from said restriction to said region of interest.

13. The apparatus of claim 11, wherein the control, by said control unit, of said collimation operation includes: a) said control unit deciding upon collimator settings for said X-ray collimator for the shaping and sizing of said aperture; and b) the actuating of said X-ray collimator to realize the decided upon collimator settings.

14. The apparatus of claim 13, further comprising said X-ray imager, and wherein said deciding upon entails comparing, as to magnitude, imager alignment data derived from said computed imager control data to current imager alignment data reflective of a spatial configuration of said imager.

15. The apparatus of claim 11, wherein the shaping and sizing by said collimation operation are dynamically responsive to the sensing by said sensor in said 3D survey.

16. The apparatus of claim 1, further comprising said X-ray source and said X-ray detector and configured such that, throughout a period of movement of said object, said imager collimation window is tracking said object and said X-ray imager is dynamically realigned in accordance with the tracking.

17. The apparatus of claim 1, wherein said demarcating entails connecting a pair from among said plurality of anatomic landmarks via a line segment, said imager collimation window being a closed figure.

18. The apparatus of claim 17, wherein said pair from among said plurality of anatomic landmarks consists of two joints in a skeleton.

19. The apparatus of claim 1, wherein said 3D image data analyzer is further configured to update said imager collimation window upon user request, the updating making use of an ongoing tracking by sensor of the object's movement in three spatial dimensions, the updated imager collimation window thereby following the object's movement, said control unit using the updated imager collimation window to control said X-ray imager during the object's movement.

20. A method comprising the steps of:
receiving 3D image data sensed by a sensor in a 3D survey of an object while said object resides between an X-ray imager's X-ray source and said imager's X-ray detector, the 3D image data so received including spatial depth information that varies with the object's outer surface, said 3D image data descriptive of the object's shape in 3D;
computing from the received 3D image data anatomical landmark data of the object to so obtain imager control data to control said imager, the computed control data including demarcation data demarcating an imager collimation window for a region of interest of said object;
using the computed control data to control operation of the X-ray imager at least one of during and before image acquisition of said object; and
updating the imager collimation window when movement of the object is detected or upon user request, the updated imager collimation window thereby following the object's movement and using the updated imager collimation window to control the imager during or in between the object's movement.

21. The method of claim 20, wherein said X-ray detector has a beam-receiving surface for receiving an X-ray beam used in said image acquisition subject to the controlled operation, said method further comprising the act of:
confining said X-ray detector to remain, throughout the controlled operation: a) within a room; and b) oriented, for receipt of X-rays from said X-ray source, so that said beam-receiving surface faces horizontally and extends vertically.

22. A non-transitory computer readable medium having stored thereon a computer program for X-ray system adjustment, said computer program having instructions executable by a process for performing plurality of acts, from among said plurality there being the acts of:
receiving 3D image data sensed by a sensor in a 3D survey of an object while said object resides between an X-ray imager's X-ray source and said imager's X-ray detector, the 3D image data so received including spatial depth information that varies with the object's outer surface, said 3D image data descriptive of the object's shape in 3D;
computing from the received 3D image data anatomical landmark data of the object to so obtain imager control data to control said image, the computed control data including demarcation data demarcating an imager collimation window for a region of interest of said object;
using the computed control data to control operation of the X-ray imager at least one of during and before image acquisition of said object; and
updating the imager collimation window when movement of the object is detected or upon user request the updated imager collimation window thereby following the object's movement and using the updated imager collimation window to control the imager during or in between the object's movement.

23. The no-transitory computer readable medium of claim 22, wherein, from among said plurality of acts, there is, for a mode of operation of said X-ray system, the act by which the controlling of said operation of said X-ray imager is performed in dynamic response to the sensing by said sensor in said 3D survey; the computing of said anatomical landmark data; the obtaining of said imager control data; and said demarcating.

24. The non-transitory computer readable medium of claim 22, wherein the updating of the imager collimation window updates the imager collimation window as to shape and size.

* * * * *